(12) United States Patent
Willness

(10) Patent No.: US 11,035,838 B2
(45) Date of Patent: Jun. 15, 2021

(54) AUTOMATED SOIL SENSOR SYSTEM ADAPTABLE TO AGRICULTURAL EQUIPMENT, TRUCKS, OR ALL TERRAIN VEHICLES

(71) Applicant: Phantom Ag Ltd., Naicam (CA)

(72) Inventor: Corwyn Willness, Naicam (CA)

(73) Assignee: Croptimistic Technology Inc., Naicam (CA)

( * ) Notice: Subject to any disclaimer, the term of this patent is extended or adjusted under 35 U.S.C. 154(b) by 472 days.

(21) Appl. No.: 15/948,420

(22) Filed: Apr. 9, 2018

(65) Prior Publication Data
US 2018/0356389 A1    Dec. 13, 2018

Related U.S. Application Data

(60) Provisional application No. 62/483,665, filed on Apr. 10, 2017.

(51) Int. Cl.

| | |
|---|---|
| *G01N 33/24* | (2006.01) |
| *B62B 15/00* | (2020.01) |
| *A01B 79/00* | (2006.01) |
| *G01N 27/04* | (2006.01) |
| *G01C 5/00* | (2006.01) |
| *G01S 19/14* | (2010.01) |
| *G01C 9/06* | (2006.01) |
| *H04W 88/02* | (2009.01) |
| *B60R 16/03* | (2006.01) |

(52) U.S. Cl.
CPC ........... *G01N 33/24* (2013.01); *A01B 79/005* (2013.01); *B62B 15/007* (2013.01); *G01C 5/00* (2013.01); *G01C 9/06* (2013.01); *G01N 27/043* (2013.01); *G01S 19/14* (2013.01); *B60R 16/03* (2013.01); *G01N 2033/245* (2013.01); *H04W 88/02* (2013.01)

(58) Field of Classification Search
CPC .. G01N 33/24; G01C 5/00; G01C 9/06; G01S 19/14; B60R 16/03
See application file for complete search history.

(56) References Cited

U.S. PATENT DOCUMENTS

| | | | | |
|---|---|---|---|---|
| 10,345,283 | B1* | 7/2019 | Laird | ..................... G01N 33/24 |
| 10,512,212 | B2* | 12/2019 | Koch | .................. G01N 27/223 |
| 2015/0305226 | A1* | 10/2015 | Zemenchik | ............ A01B 63/32 |
| | | | | 701/50 |
| 2018/0356389 | A1* | 12/2018 | Willness | .............. A01B 79/005 |

(Continued)

FOREIGN PATENT DOCUMENTS

| | | |
|---|---|---|
| CA | 2392962 A1 | 1/2003 |
| CA | 2663917 A1 | 10/2010 |
| WO | WO2015/164802 A1 | 10/2015 |

*Primary Examiner* — Jamel E Williams
(74) *Attorney, Agent, or Firm* — Gordon & Jacobson, P.C.

(57) ABSTRACT

The invention relates to the analysis of field characteristics to help determine prescriptions for crop input levels. A non-conductive enclosure houses a mapping system. The enclosure has a rectangular base and four walls extending from the base. A removable cover is received by the four walls. A foam interior receives at least one conductivity sensor. A port receives at least one electrical connection from an agricultural equipment in order to interface with the mapping system. A mounting assembly may mount the non-conductive enclosure to the agricultural equipment.

58 Claims, 11 Drawing Sheets

(56) References Cited

U.S. PATENT DOCUMENTS

| | | | | |
|---|---|---|---|---|
| 2019/0257809 A1* | 8/2019 | Ellegaard | ............... | G01N 33/24 |
| 2019/0285608 A1* | 9/2019 | Laird | ................. | G01N 21/3563 |
| 2019/0289775 A1* | 9/2019 | Maxton | ................ | A01B 79/005 |
| 2020/0093054 A1* | 3/2020 | Aesaert | ............. | A01D 41/1274 |

* cited by examiner

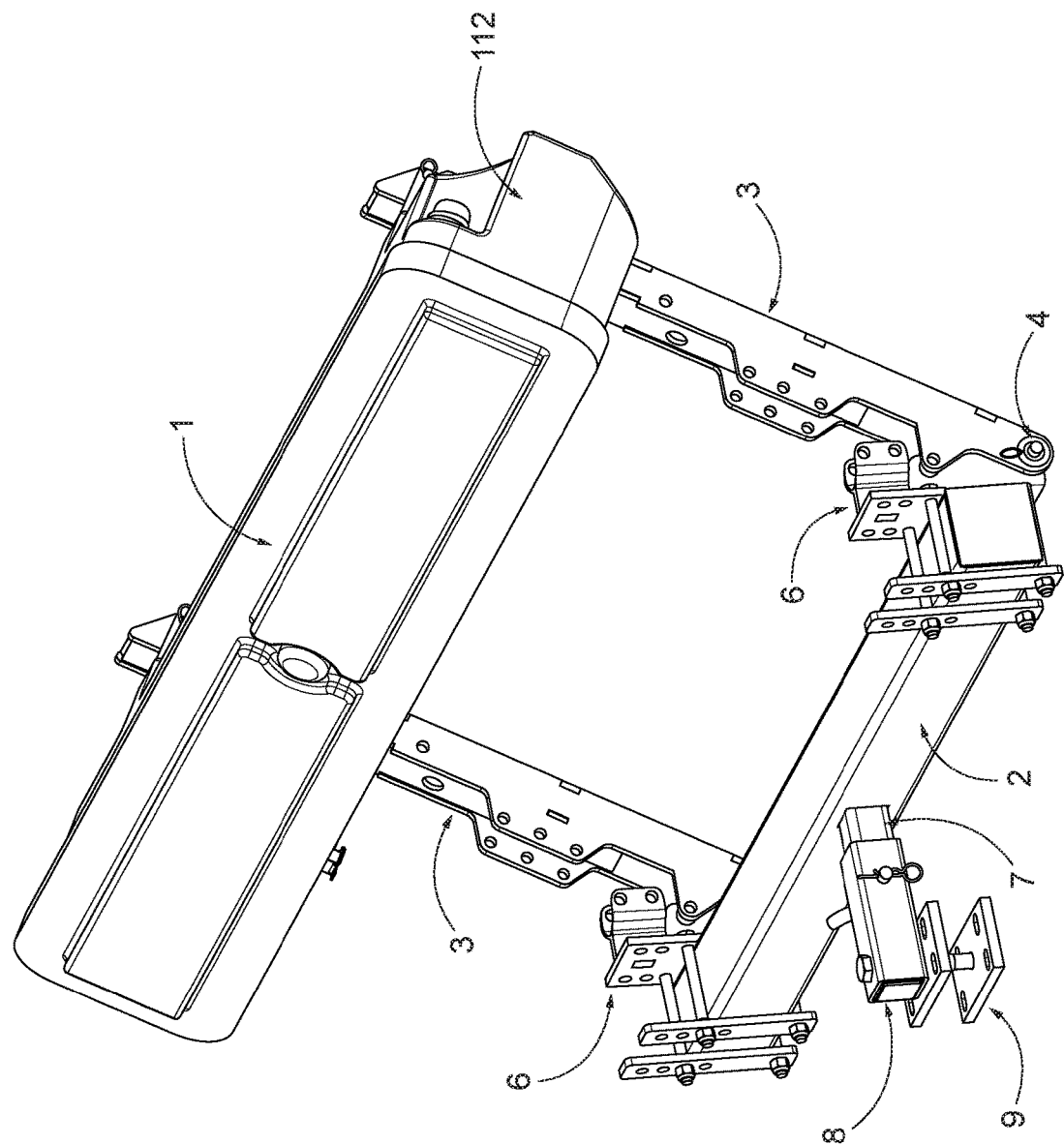

AUTOMATED SOIL SENSOR SYSTEM ADAPTABLE TO AGRICULTURAL EQUIPMENT, TRUCKS, OR ALL TERRAIN VEHICLES

CROSS-REFERENCE TO RELATED APPLICATION

This application claims the benefit of U.S. provisional application Ser. No. 62/483,665, filed on Apr. 10, 2017, which is hereby incorporated by reference herein in its entirety.

FIELD OF THE INVENTION

The invention relates to methods and systems for the analysis of field characteristics to help determine prescriptions for crop input levels. In particular, the invention relates to measurement and data collection of field characteristics in a frequent and/or unobtrusive manner.

BACKGROUND

The productivity demands on agricultural land are increasing and therefore requiring new and enhanced methods for extracting greater yield and grain quality from existing fields. Increased global environmental concerns prompt agricultural practices to recognize that air, water, and soil stewardship as important as safe and healthy food production. This has resulted in the development and deployment of various enhancement technologies, such as more effective fertilizers and methods for treating fields. While these new technologies and methods may increase productivity, they also introduce additional cost that can be prohibitive if not managed properly.

An additional complicating factor is that a particular field is not normally uniform in characteristics across its entire extent. Variations in soil type and conditions, elevation, water flow patterns and the like mean that different areas of a target field may require different treatment levels to achieve a target productivity. Treating a target field as a uniform entity may result in overuse of crop inputs in some areas and accordingly an undue expenditure and environmental liability. Under-application in some areas may result in wasted resources of sunlight and water as well as lost profitability.

Various methods and systems have been taught for measurement and analysis of field variability in determining a target crop input level based on a defined end goal. Some solutions perform variable rate mapping services by satellite imagery due to the lower upfront equipment, maintenance, and resource costs per acre. For example, Canadian Patent No. 2,392,962 to Hanson teaches a method that employs satellite imagery to determine crop density, which in turn is used to identify yield potential. Yield potential and soil conductivity measurements are used to define management zones, which are then utilized to illustrate condition variability across a target field, and soil samples are taken for each of the identified management zones. The stated purpose of Hanson is to reduce the number of soil samples required for a target field, as sampling costs can be significant in large fields.

As a further example, Canadian Patent Application No. 2,663,917 to Schmaltz and Melnitchouk teaches the use of satellite imagery to determine differences in plant biomass densities across a target field. This allows the identification of plant production zones, which are grouped into soil management zones. For each soil management zone, residual nutrients in the soil are compared against an optimal target level, with any shortfall subsequently used in providing a crop input prescription for each zone in the target field.

However, it has been found that satellite methods may not always provide an optimal crop input prescription that places emphasis on the conditions most likely to influence yield in a particular target field that has variability largely due to soil, water, and topography.

An alternative to satellite imagery may be heavily modified half-ton trucks equipped with specialized sensors and equipment and in-cab monitors in order to map fields. The trucks require trained operators to transport the truck to and throughout fields in geographically distant locations during a compressed fall and spring mapping season. The equipment, maintenance, and resource investment required to provide variable rate mapping service using trucks may be high. As well, the window of opportunity to map fields may be limited to after harvest and prior to seeding. Mapping in the winter is not possible due to snow cover preventing the trucks from traversing the field and preventing identification of critical topography features needing to be driven over. Wet weather may also reduce the time available for mapping in a given year due to farmers not wanting deep ruts in their fields. Due to these limitations a single mapping truck is typically limited to mapping 15,000 to 25,000 acres per year. In addition, there is a small risk of transporting soil or crop disease and weeds from farm to farm with mapping trucks being in contact with a variety of fields and regions.

In another example, International Patent Pub. No. WO/2015/164802 to Zemenchik et al. discloses the use of an agricultural implement as a platform for soil sensor data collection. The mounting assembly includes a ramp to move the analyzer rearwardly and proximate to the surface of the agricultural field. The analyzer can be coupled to an analyzer member that rolls down the back of the ramp, which is coupled to a rear hitch. A wheel or sled can support the analyzer member against the surface of the field while the analyzer is positioned proximate to the surface of the field. The analyzer member may be coupled to the ramp via a cord and pulley system to return the analyzer and the analyzer member to the ramp for storage and transportation.

Other platforms for carrying a soil electrical conductivity sensor and mapping fields such as Unmanned Aerial Vehicles (UAV) have been researched. Results show the quality of the data collected using this method is currently limited by the recording and accuracy of the flight height. As well, current regulations limit the use of an UAV to within sightlines of the operator so there would be limited potential to save labor resources using a UAV for a data collection platform.

SUMMARY OF THE INVENTION

According to one aspect described herein, there is provided a mounting assembly for mounting a mapping system to an agricultural equipment. The mounting assembly may comprise: one or more support arms extending from the agricultural equipment and configured to pivot the support arm(s) with respect to the agricultural equipment; and a non-conductive sensor enclosure positioned along the support arm(s). The support arm(s) may be pivotally coupled to a main beam mounted horizontally with respect to the agricultural equipment. The support arm(s) may comprise a pair of support arms pivotally coupled on each end of the main beam. One or more shock absorbers may be coupled between the support arm(s) and the main beam.

According to an aspect, one or more mounting brackets may comprise a series of vertically arranged holes. The series of vertically arranged holes may receiving one end of the shock absorber(s); and the other end of the shock absorber(s) may be received in one or more holes on the support arm(s). a position of the sensor enclosure with respect to a soil surface and the agricultural equipment may be determined by a shock absorber position of the at least one shock absorber within the series of vertically arranged holes. The support arm(s) may position the sensor enclosure between about 15 cm to about 76 cm above a soil surface and may position the sensor enclosure between about 61 cm to about 91 cm behind the main beam.

According to another aspect, the shock absorber(s) may reduce vertical acceleration and may provide relief when the sensor enclosure contacts the soil surface, such as a rock, etc.

In some aspects, a hitch receiver may be coupled to the main beam for coupling the main beam to the agricultural equipment by way of a hitch.

In some aspects, the support arm(s) may be integrally formed with the sensor enclosure. The sensor enclosure position along the support arm(s) may be adjusted via a series of pins and holes along the at least one support arm. The support arm(s) may be pivoted fully upwards and pinned into a transport position for road travel. The sensor enclosure may comprise a removable cover. The sensor enclosure may comprise a foam interior.

According to all aspects herein, the mapping system may comprise a power supply, one or more external sensors, and a data acquisition system. The power supply may comprise an uninterruptable power supply circuit. The uninterruptable power supply circuit may comprise an internal battery and a charger. The data acquisition may perform a controlled shutdown upon loss of power supplied from the vehicular power source. The power supply may provide power to the at least one external sensor. The one or more external sensors may provide measurement data to the data acquisition system. The data acquisition may store measurement data on a tangible computer-readable medium. The data acquisition system may transmit the measurement data over a wireless connection (e.g. one or more wireless transceivers) to one or more computer servers. The wireless transceiver may comprise at least one of a Wi-Fi transceiver, a Bluetooth transceiver, a 3G transceiver, a 4G transceiver, an LTE transceiver, or a proprietary wireless transceiver. The external sensors may comprise at least one of: a soil electrical conductivity sensor, a height sensor, a tilt sensor, and a GPS receiver.

The mapping system may comprise a power supply and a data acquisition system. The power supply may comprise an uninterruptable power supply circuit. The uninterruptable power supply circuit may comprises an internal battery and a charger. The data acquisition may perform a controlled shutdown upon loss of power supplied from the vehicular power source. The power supply may provide power to at least one external sensor. The external sensor may provide measurement data to the data acquisition system and/or may store measurement data on a tangible computer-readable medium. The data acquisition system may transmit the measurement data over a wireless connection to at least one computer server.

According to one aspect described herein, there is provided a mounting assembly for mounting a soil electrical conductivity mapping system to an agricultural implement. The mounting assembly may comprise a non-conductive tow beam coupled to the agricultural implement at one end using an attachment assembly that permits vertical pivoting of the beam; and a sled coupled to the non-conductive tow beam at another end via a spherical coupler. The sled may comprise a base and a housing for the mapping system. The housing may comprises a removable cover and/or the housing may further comprise a foam interior to protect the components inside the sled.

A vehicle power source may be electrically coupled to the mapping system through the spherical coupler. The non-conductive tow beam may be selected from at least one of a rigid wood, a plastic, and a composite material. In some aspects, the non-conductive tow beam may be extendable and/or may have a length of 6 to 12 feet.

The attachment assembly may comprise at least two fastening means. One of the fastening means may be configured to attach to a beam of the agricultural implement and another one of the fastening means may be configured to attach to a hitch at the rear of an agricultural implement. The attachment assembly may resemble a trapezoidal pyramid. The attachment assembly may further comprise a recessed portion along the trapezoidal pyramid for receiving the non-conductive tow beam. The recessed portion may limit motion of the non-conductive tow beam to a vertical rotational motion. A pair of holes on either side of the recessed portion may receive a pin passing through the non-conductive tow beam.

The sled may further comprise at least two skids fastened to a bottom of the base. The skids may comprise an ultra-high molecular weight material and/or may be replaceable. The sled may further comprise a ramp at a front end of the sled. The ramp may have a slope between 10-degrees and 40-degrees. The skids may slope upwards at the front end and a back end of the sled. The slope of the ramp may match the slope of the skids at the front end of the sled.

According to some aspects, the spherical coupler may permit the sled to rotate 360-degrees in a horizontal plane to facilitate reversing of the agricultural implement.

Other aspects and combinations may be apparent to one of skill in the art on reading the present disclosure.

DESCRIPTION OF THE DRAWINGS

While the invention is claimed in the concluding portions hereof, example embodiments are provided in the accompanying detailed description which may be best understood in conjunction with the accompanying diagrams where like parts in each of the several diagrams are labeled with like numbers, and where:

FIG. 1A is a perspective view of a mounting assembly in a transport position and enclosure for an automated soil sensor system adaptable to agricultural equipment;

FIG. 4, is a block diagram of an example electronic system for implementing the mapping system;

DETAILED DESCRIPTION OF THE ILLUSTRATED EMBODIMENTS

Farmers travel over their fields multiple times per year with various agricultural equipment including at least tractors, tillage tools, harrows, air seeders, fertilizer applicators, liquid fertilizer carts, anhydrous ammonia carts, sprayers, tillage implements, windrowers, combines, all-terrain vehicles, trucks, or any other implement being towed over fields. If the data collected during the mapping process (e.g. electrical conductivity, latitude, longitude, elevation) may be collected during these operations that would provide greater mapping capacity at a potentially lower cost per acre, more time available for mapping, and a lower fuel cost. Agricultural equipment may also be better optimized to travel over wet fields allowing mapping to still occur in adverse conditions. Moreover, the risk of transporting soil or crop disease and weeds may be mitigated by using the farmer's own implement as the field mapping platform. As a result of these factors, the farmer may have improved access to a field mapping service at a potentially lower cost.

It is an aspect of the embodiments described herein to provide an easily installable, low maintenance mapping system that may be part of a fleet of systems. The easily installable mapping system may be provided on the seeding equipment prior to seeding in early spring. Once that farmer is completed seeding, the mapping system may be removed by the farmer or a technician and may be available for use by another farmer and/or for use on other agricultural equipment. The mapping system may perform all functions independently and may not interfere with the regular operation of the seeding equipment or any other agricultural equipment that the mapping system may be mounted to.

The installable mapping system may be installed on agricultural equipment such that the electrical conductivity, location, elevation field data, and/or any combination thereof may produce variable rate fertilizer and seeding maps. The mapping data may be collected while the agricultural equipment passes over their fields. It may be estimated that one of the mapping systems described herein may add 10,000 to 50,000 acres of mapping capacity per year depending on how many types of agricultural equipment the mapping system may be installed on.

As well, agricultural equipment manufacturers may offer a field mapping system as an option on their agricultural equipment. For example, seeding equipment manufacturers may benefit from having a superior field mapping service available that may complement the variable rate seeding equipment that is sold to farmers. The field mapping system configured to be mountable to seeding equipment is described herein. The field mapping system described may be applied equally well to other agricultural equipment, trucks, or all-terrain vehicles.

Figure 1B:
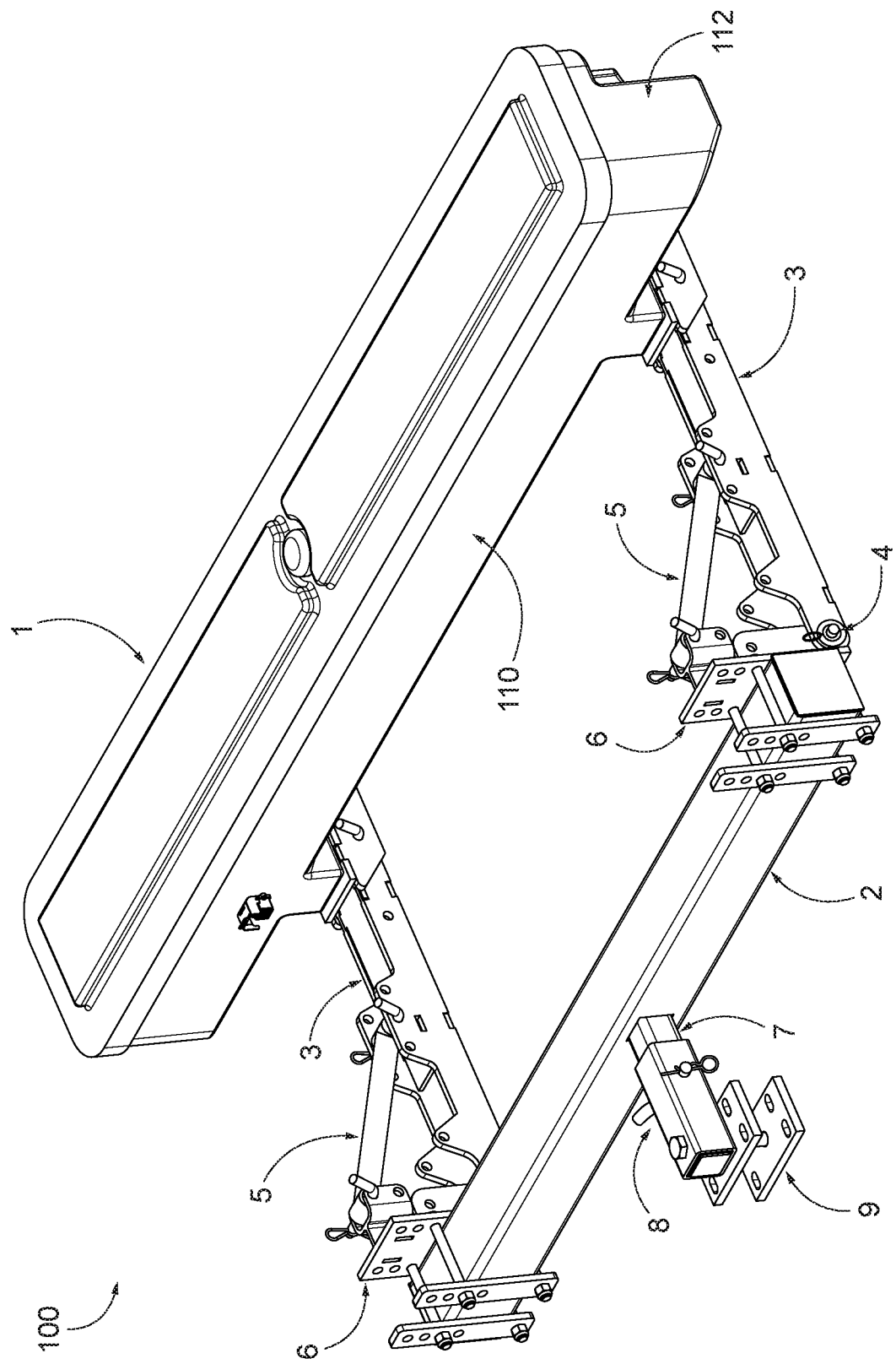
FIG. 1B is a perspective view of the mounting assembly in an operating position and enclosure for the automated soil sensor system adaptable to agricultural equipment.
Figure 2:
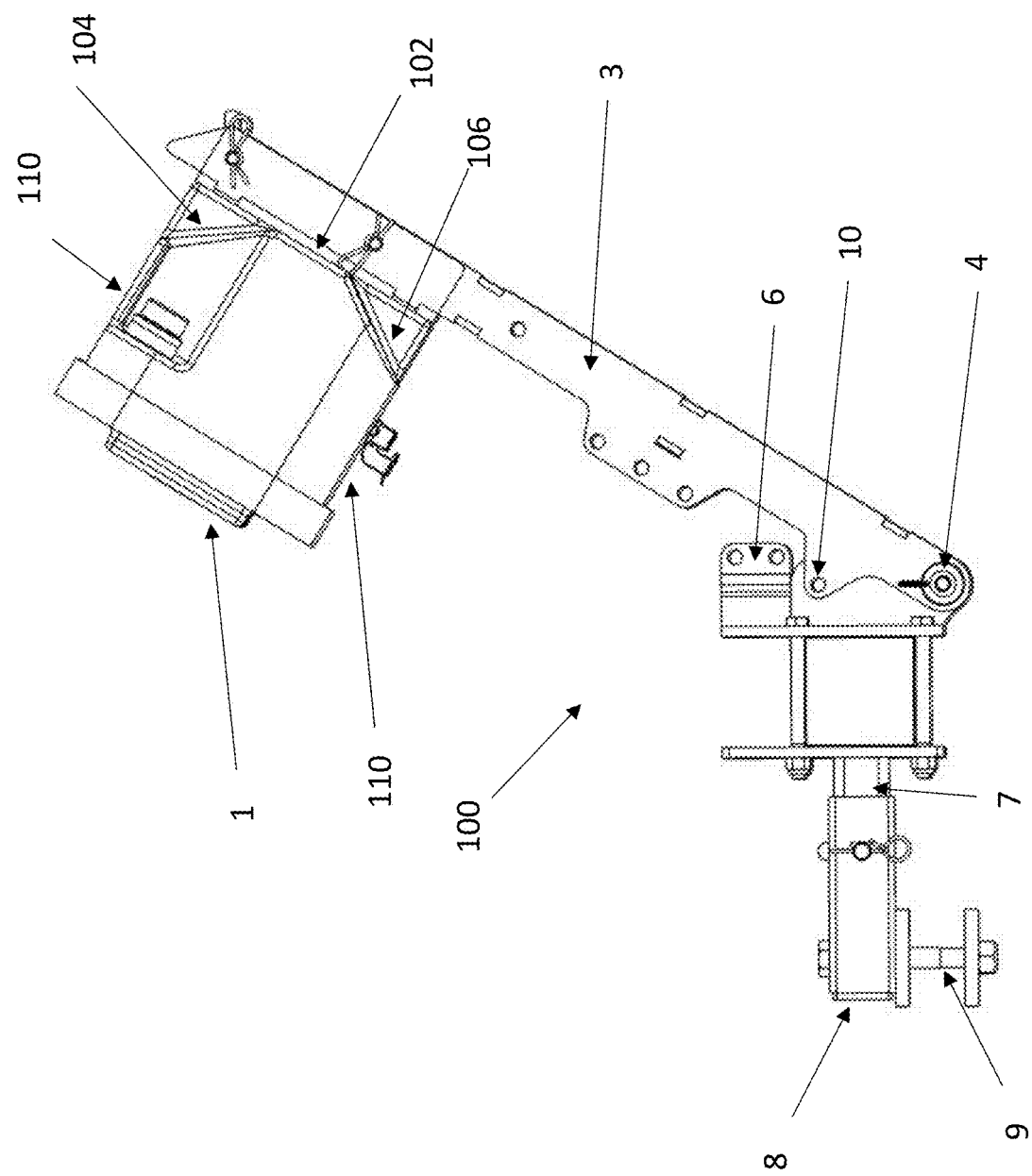
FIG. 2 is a perspective view of the mounting assembly and enclosure folded up into transport position.

FIGS. 1A and 2 show a mounting assembly 100 in a transport position (FIG. 1) and an in-use or operating position (FIG. 1B). The mounting assembly may be comprised of a series of structural members that may locate a sensor enclosure 1 above a soil surface by between about 15 cm to about 76 cm and about 61 cm to about 91 cm rear of a main structural beam 2. In other aspects, the sensor enclosure 1 may be located between about 76 cm and about 106 cm from the main structural beam 2. This range may be achieved by adjusting a position of the sensor enclosure using mounting brackets 6 and/or different pin positions 3 for shock absorbers 5 as described in further detail below. The main beam 2 may be horizontal with respect to the agricultural equipment. At least one support arm 3, in this aspect two support arms, may support and be removably coupled to the sensor enclosure 1. In this aspect, the support arms 3 may be coupled to the sensor enclosure using pins. The support arms 3 may be formed from steel, aluminum, rigid wood, plastic, or composite materials. In other aspects, the two support arms may be integrally formed with the sensor enclosure 1.

The support arms 3 may be pivotally coupled to the main structural beam 2. The length of the support arms 3 may vary depending on the type of agricultural equipment. The length may be a sufficient distance from the conductive material of the agricultural equipment in order to minimize interference with the measurements. The support arms 3 may allow the sensor enclosure 1 to pivot up and down with respect to the main structural beam 2 about one or more pins 4 on a common pivot axis. The pivot range may allow for adjustment of a sensor height and may provide relief in case of contact of the enclosure 1 with the soil surface or rocks lying thereon. One or more shock absorbers 5 may dampen a pivot motion of the enclosure 1 so as to reduce vertical acceleration resulting from a host vehicle traveling over rough fields.

Two mounting brackets 6 at either end of the main structural member 2 may serve as the support arm 3 pivot point, a location of a top pin of the shock absorber 5, and may provide height adjustment of the sensor enclosure 1 via a series of vertically arranged holes. The sensor enclosure 1 may be adjusted fore or aft via a series of pins and holes at a rear of the support arms 3. This fore or aft adjustment may allow for the sensor enclosure 1 to be placed nearer or further from conductive materials of the host vehicle. When the electrical conductivity data is significantly affected by the conductive materials of the host vehicle, then the sensor enclosure 1 may be placed further from the conductive materials. The square tube 7 may be welded to the main structural tube 2 and may be inserted into a hitch receiver tube assembly 8 and secured in place. In the case of mounting to agricultural equipment, an additional washer plate 9 may be used to secure the hitch receiver tube assembly 8 to a rectangular structural member or hitch tab of the agricultural equipment.

FIG. 2 shows the mount assembly 100 and the sensor enclosure 1 in a non-operating or transport position. The transport position may place the sensor enclosure 1 and support arms 3 away from the soil and rocks that could damage the enclosure 1 when transporting the agricultural equipment, truck, or all-terrain vehicle at high speeds. To place the assembly 100 into transport position, the shock absorber 5 may be removed and the support arms 3 may be pivoted upwards about the pivot pins 4 until the upper shock locating pins may be inserted into one or more transport pin holes 10. In the transport configuration, the sensor enclosure 1 may be approximately 1.1 m above the ground.

Figure 3:
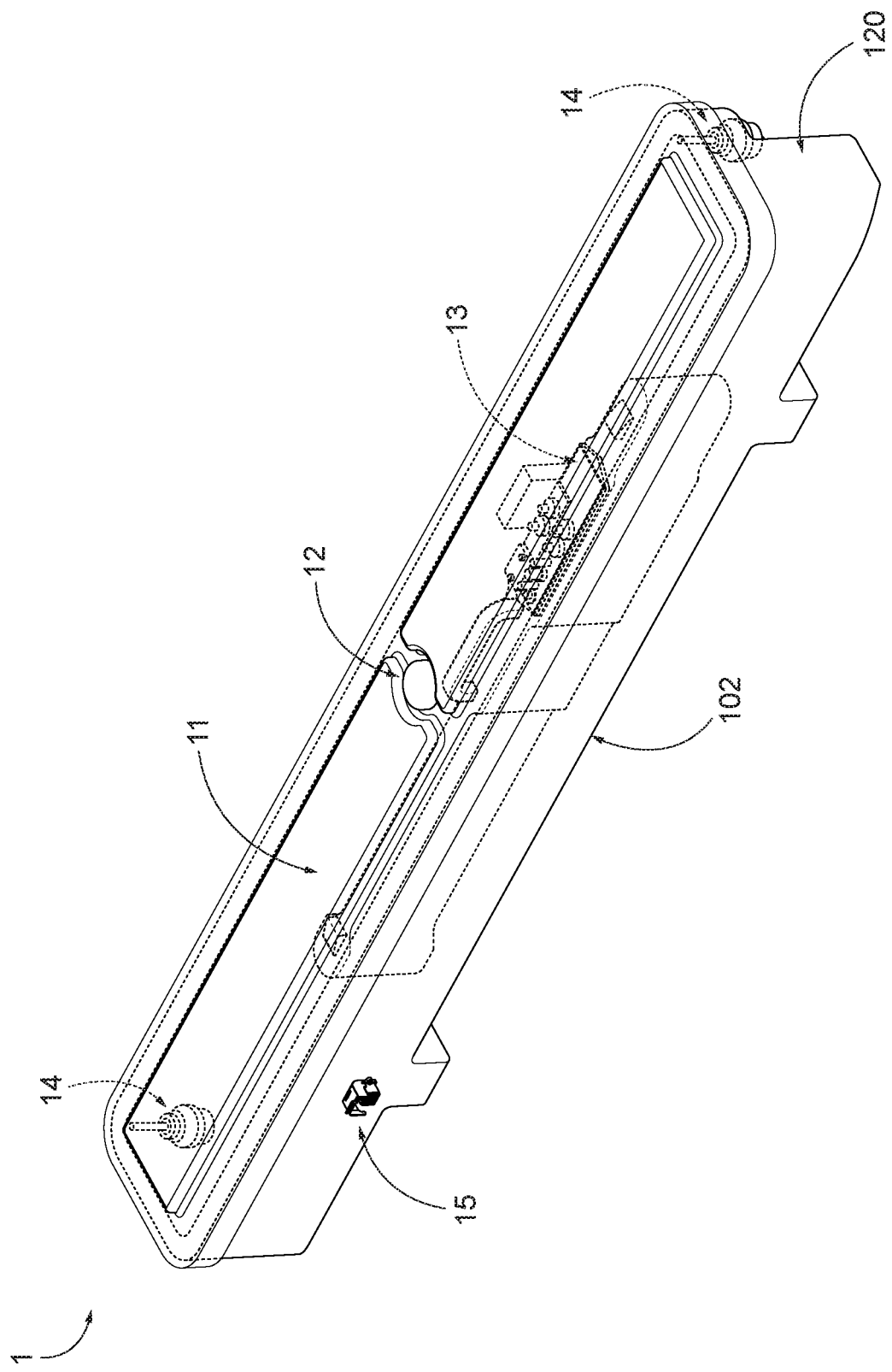
FIG. 3 is a perspective view of the enclosure and internal sensors.

FIG. 3 shows the sensor enclosure 1 removed from the mount assembly 100. The sensor enclosure 1 may comprises a base 102 coupled to (or integrally formed with) four walls 110, 112 extending from the base 102. The four walls 110, 112 may comprise two short walls 112 and two long walls 110 so that, when combined with the base, form a generally rectangular-shaped enclosure. The sensor enclosure 1 may be constructed from a non-conductive plastic or other non-conductive material. The sensor enclosure 1 may additionally be protected by replaceable sheets of an ultra-high molecular weight material. In some aspects, the enclosure 1 may further comprise a slope at a front 106 and/or rear 104 of the base 102. The slopes 104, 106 may be in the range of 10-degrees and 40-degrees. In some aspects, the front slope 106 may be equal to the rear slope 104. In other aspects, the front slope 106 may be less or greater than the rear slope 104. In some aspects, the front slope 106 and/or rear slope 104 may comprise only a portion of the base 102.

The sensor enclosure 1 may include a removable lid 11 which also may include a GPS sensor 12 placed in a recession on the top of the removable lid 11. A soil electrical conductivity sensor 13 may be housed inside the sensor enclosure 1. A series of foam or rubber bumpers (not shown) around the walls 110, 112 and the base 102 may secure a soil electrical conductivity sensor 13 in place and provide cushioning for the conductivity sensor 13 when traveling over rough fields. One or two height sensors 14 may be located at or near rear outside corners of the sensor enclosure 1. In this aspect, the height sensor 14 may be placed in a recess and may be positioned from the wall 112 by way of a flange 120. The height sensors 14 may provide soil sensor height data corresponding to a distance between the enclosure 1 and the ground.

Since the quality of soil electrical conductivity measurements may be affected by sensor height off of the ground. Therefore the sensor height data may be used to improve conductivity measurements, such as when the sensor height data is outside of an acceptable range. The acceptable height range may vary with each installation and therefore the acceptable sensor height range may be determined at installation time. The height may be automatically reported and recorded to the data acquisition system and an installer may view the electrical conductivity measurements and height data to determine an acceptable sensor height range for each installation. In another aspect, instead or in addition to the height sensor, a tilt sensor may provide tilt data in order to calculate the tilt of the electrical conductivity sensor with respect to the ground or the agricultural equipment.

A port 15, such as a bulkhead Ethernet connector, may provide electrical connections for powering all sensors in the enclosure 1 and data transfer to an electronics housing where the data acquisition system may be located. In this aspect, the port 15 passes through a wall 110, 112 of the enclosure 1. A multi-port USB extender (not shown) may also be housed inside of the sensor enclosure 1. The USB extender may provide a central connection point for all sensors in the enclosure 1 and may allow for additional or alternative sensors.

Figure 4A:
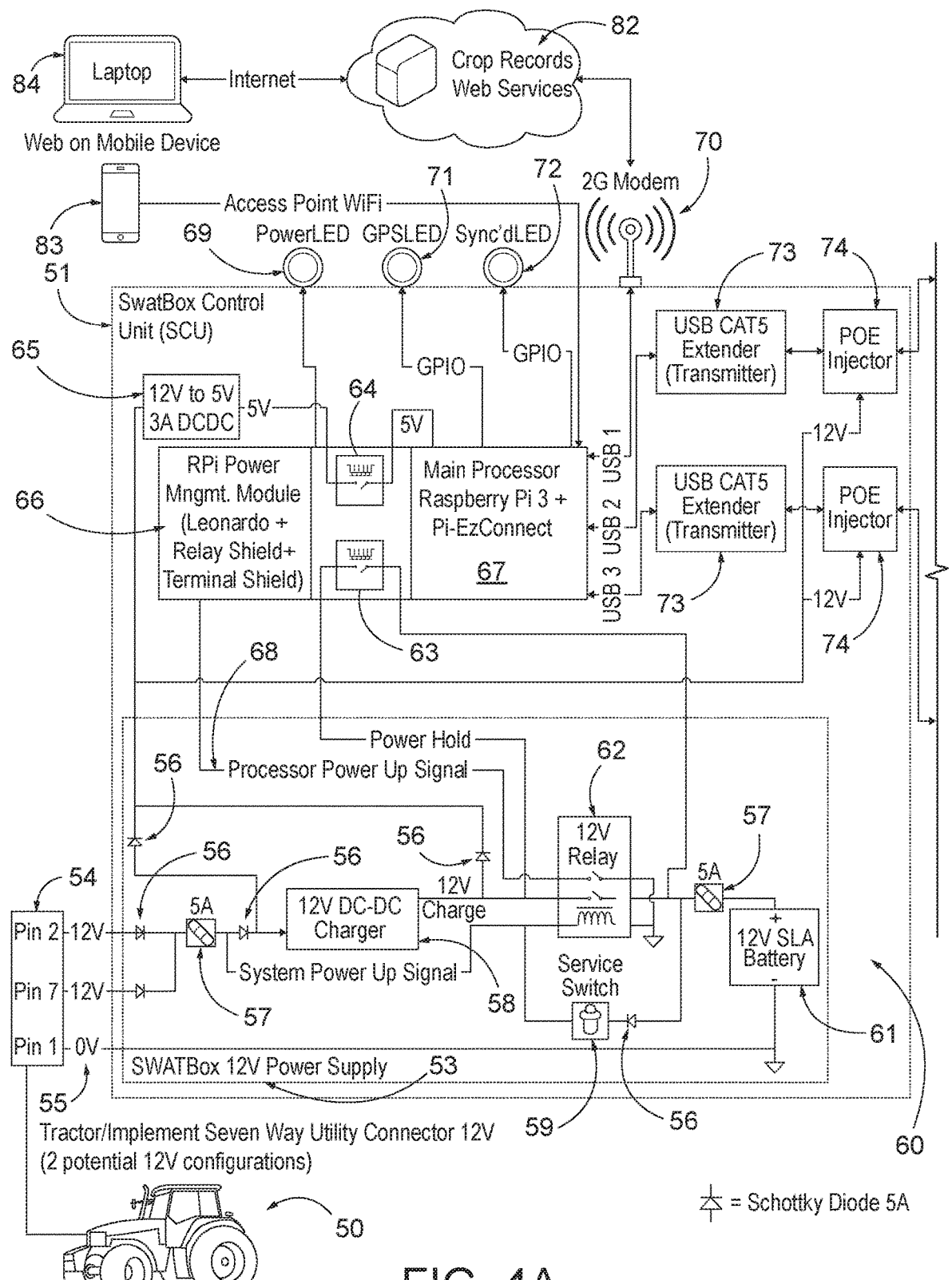
FIG. 4, which is presented in two parts, FIG. 4A and FIG. 4B, which together comprise
Figure 4B:
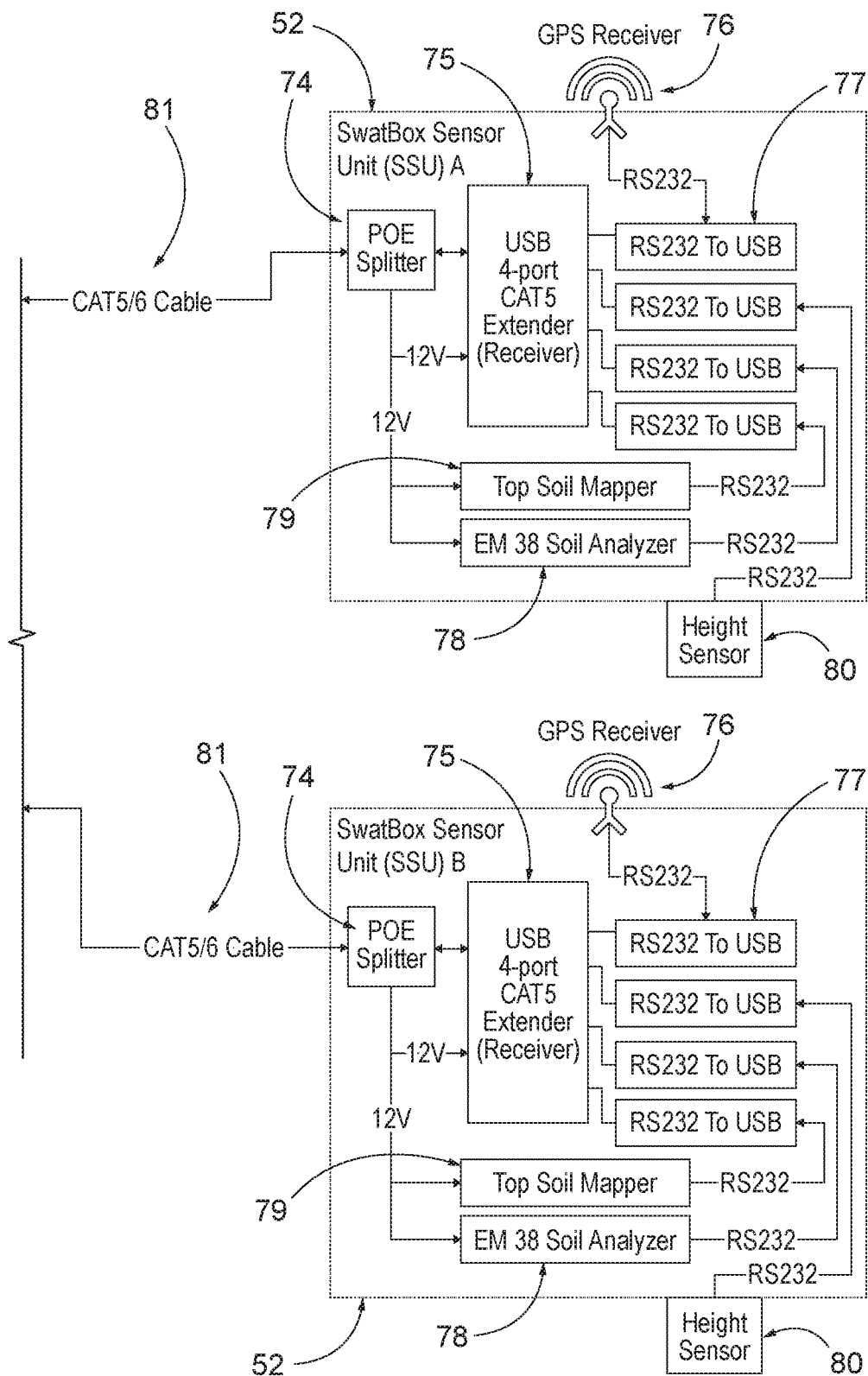

Turning now to FIG. 4, a block diagram of a mapping system is presented. The electronics enclosure 51 houses the electronics system that may receive 12-Volt electrical power from a tractor, implement, truck, or all-terrain vehicle 50 via a 7-way vehicle utility connector 54. The length of electrical power cable 55 may be interchangeable to accommodate varying installations. The electronics system of the electronics enclosure 51 may be divided into a power supply 53 and a data acquisition system 60.

In this aspect, the power supply 53 is an uninterruptable power supply circuit. For the power supply 53, in order to protect the data acquisition system 60, a 5-Amp fuse 57 may be provided on the power input 54 and/or an internal battery 61. One or more Schottky Diodes 56 may protect the data acquisition system 60 in the event that the power input 54 should accidentally be reversed and to prevent back feeding. The power input 54 may be connected to a 12-Volt DC-DC charger 58 that may charge the 12-Volt internal battery 61. The power input 54 may also provide a system power up signal to a 12-Volt relay 62 that connects the internal battery 61 to the charger 58 and data acquisition system 60 when system power is supplied. Conversely, the 12-Volt relay 62 supplies power to the data acquisition system 60 when the system power is not supplied. The internal battery 61 may allow for a controlled shutdown of the data acquisition system 60 when external power is removed. The internal battery 61 may also act as a service and maintenance power source for when no external power is applied.

A micro-controlled relay 63 may be used as a controlled power hold so that when the 12-Volt supply 54 is removed, the 5-Volt power 65 remains on to supply the data acquisition system 60 from the internal battery 61. A service switch 59 may be used to manually power up the data acquisition system 60 for service and maintenance. In some aspects, the power supply 54 may automatically supply the required power to the data acquisition system 60 without requiring a separate power up or down procedure other than turning a key on the tractor or truck 50 on or off.

The power supply 54 may provide a 12-Volt output to a 12V-to-5V DC/DC regulator 65. A 5-Volt regulated output of the DC/DC regulator 65 may be used to power a power management module 66 that controls the power management functions of the Raspberry Pi™ acquisition system 67 via a micro controlled relay 64. A power up signal 68 may be a switched line that indicates the main processor 67 (e.g. Raspberry Pi™ or equivalent) needs to power up or power down. This power up signal closes when external 12-Volt supply 54 may be applied and opens when external 12-Volt supply may be removed. An internally controlled signal to the micro-controlled relay 63 may be used to energize the relay (e.g. power hold). The micro-controlled relay 63 may be enabled on power up and remains enabled until power to the main processor 67 may need to be removed. This allows the data acquisition system 60 to power down in a controlled manner after the external 12-Volt supply 54 is removed. When the power management module 66 becomes active, a power status light-emitting diode (LED) 69 becomes active and may use a sequence of flashes to indicate a state of the main processor 67. Although the regulator 65 and the power management module 66 are depicted as part of the data acquisition system 60, other aspects may have the regulator 65 and/or the power management module 66 within the power supply 53. In other aspects, the power management module 66 may be external to a main processor 67 or housed within the main processor 67.

The main processor 67, in this aspect a Raspberry Pi™ 3, may execute instructions from a tangible computer-readable medium (not shown) in order to control the data acquisition functions of the data acquisition system 60. The main processor 67 may comprise a number of general purpose input/output (GPIO) ports and/or may comprise a number of universal serial bus (USB) ports for communication with various peripheral devices. For example, the main processor 67 may receive various external sensor measurements of the field from one or more connected sensor units 52 connected to a USB port via USB-over-Ethernet extender transmitters 73 and receivers 75. A 12-Volt power may be transmitted to the sensor unit 52 with Power-Over-Ethernet injectors 74 via Ethernet cable 81 for allocation of power to the USB-over-Ethernet extender receiver 75 and various sensors 78, 79. Various lengths of Ethernet cable 81 may be used to accommodate different installations of multiple sensor units 52.

The main processor 67 may receive Global Positioning System (GPS) coordinates from a GPS receiver 76. When the GPS receiver 76 has locked onto the GPS satellites, the main processor 67 may indicate that the GPS has locked by activating a GPS status LED 71 connected to an output of the main processor 67 via GPIO. The main processor 67 may also be connected to a mapping sensor 78, 79 via a USB-over-Ethernet connection 73. In this aspect, the connection may be coupled to a USB-to-RS232 adapter 77 or other conversion adapter for communication with an EM38 soil analyzer 78 and/or a Top Soil Mapper 79, or other soil electrical conductivity sensor. The main processor 67 may also be connected to a height sensor 80 via a USB-over-Ethernet connection 73. In this aspect, the connection may be coupled to a USB-to-RS232 adapter 77 or other conversion adapter for communication with a height sensor 80.

During operation, the main processor 67 may sample the height sensor 80. In some aspects, the height sensor 80 may be sampled at a rate of 10 samples per second. In other aspects, the sampling rate may be lower such as 5 samples a second or 1 sample every minute. The main processor 67 may also receive GPS coordinates, and sample the sensors 78, 79, 80 at a sufficient rate based on a number of factors such as host vehicle velocity (e.g. 0.5-40.0 km/h) and/or desired mapping resolution. In some aspects, the GPS coordinates and sampling of the sensors 78, 79, 80 may be 0-Hz for when the host vehicle is travelling at a velocity of less than 0.5 km/h in order to prevent logging of redundant data. In other aspects, the GPS coordinates and sampling of the sensors 78, 79, 80 may be in the range of 0.5 to 5-Hz. As described herein, all measurements recorded by the main processor 67 are referred to as measurement data. In some aspects, the main processor 67 may store the measurement data within a tangible computer-readable medium (not shown) such as a Secure Digital (SD) memory card, or USB flash memory. In other aspects, the main processor 67 may stream the measurement data via a USB connection to a cellular modem 70 to wirelessly transmit the measurement data to a web server 82. In yet another aspect, the main processor 67 may store the measurement data locally within a tangible computer-readable medium and then transmit the measurement data periodically over the cellular modem 70 to the web server 82, such as, for example, when data costs may be lower or when the cellular modem 70 is within range of a cellular data tower (not shown). In even another alternative, the main processor 67 may wirelessly stream the measurement data via a Wi-Fi access point or Bluetooth® to an application executing on a mobile device 83. The mobile device 83 may then relay the measurement data over its own data connection. In some aspects, the main processor 67 may additionally compress and transmit the measurement data in order to save on cellular data costs and/or in order to maximize usage of the tangible computer-readable medium.

In other aspects, the application executing on the mobile device 83 may connect to the Wi-Fi or Bluetooth access point provided by the main processor 67. The application may enable control of the data acquisition settings such as sampling rate, which sensor to enable, troubleshooting, diagnostics, software updates, etc. The application may also be used to access the measurement data stored within the tangible computer-readable medium.

The web server 82 may comprise a cloud storage server that enables access to the measurement data for a particular field via a laptop 84 over the Internet. The web server 82 may also comprise LIDAR data gathered by contracted fixed wing aircraft for the georeferenced field elevation and topography. The web server 82 may permit real-time or near real-time access to the measurement data being collected. The web server 82 may generally comprise a processor, memory, one or more communication interfaces, and a computer-readable medium such as a hard disk drive or the like. The web server 82 may also permit real-time or near real-time remote access to the control unit 51 via cellular connection for remote service and maintenance access.

Although the aspects described herein discuss a cellular modem for data communication and a cellular antenna, other aspects may have an LTE data communication system, 3G data communication system, or other wireless communication system known in the art. In other aspects, the communication system may have one or more of a Wi-Fi transceiver, a Bluetooth transceiver, a 3G transceiver, a 4G transceiver, an LTE transceiver, or a proprietary wireless transceiver.

Although the aspects described herein discuss the support arms 3 pivotally coupled to the main support beam 2, other configurations may have the support arms 3 pivotally coupled directly to the agricultural equipment.

Although the aspects described herein discuss the support arms 3 being of a fixed length, other aspects may have the support arms 3 capable of telescoping or extendable allowing the farmer to easily extend the support arms 3 depending on the type of agricultural equipment.

Figure 5:
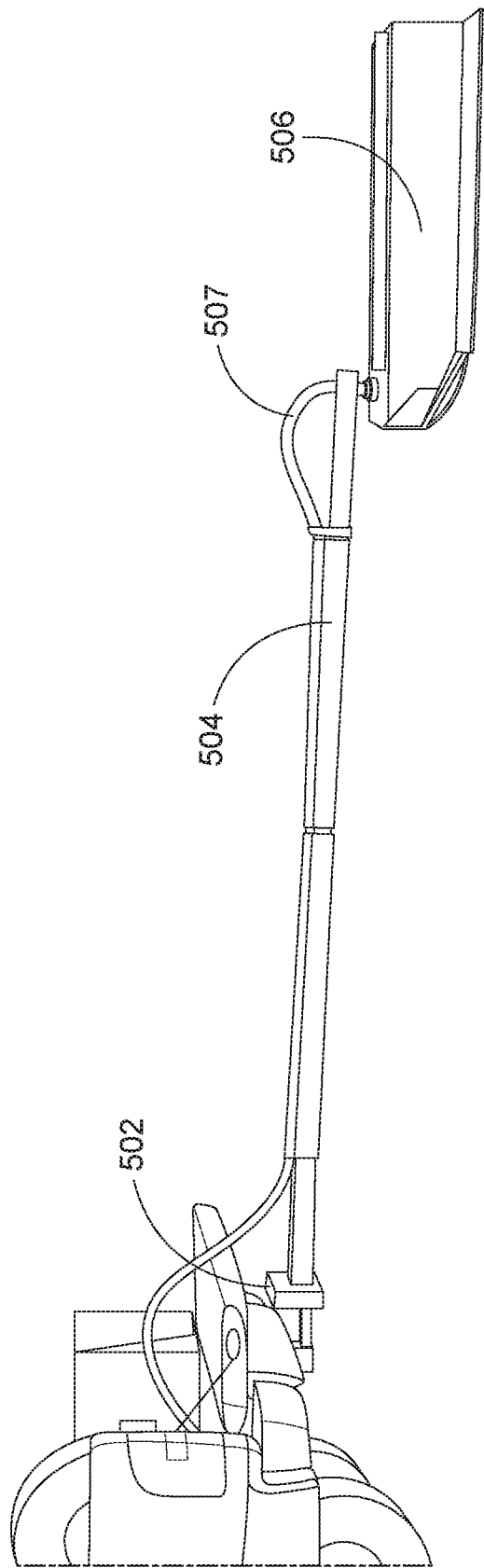
FIG. 5 is a perspective photograph of a tow beam and a sled of a mapping system for an agricultural implement.

Turning to another aspect presented in FIG. 5, a mounting assembly comprising a non-conductive tow beam 504, such as rigid wood, plastic, or composite material, may allow a sled 506 to be towed behind the agricultural implement. The non-conductive tow beam 504 may keep the sled 506 at a fixed distance away from conductive components (e.g. steel) of the agricultural implement. A length of tow beam 504 may vary depending on the implement to which the tow beam 504 is being adapted. The length of the tow beam 504 may be a sufficient distance from the conductive material of the implement in order to minimize interference with the measurements during turning of the implement. According to an aspect, the tow beam 504 may be approximately 8 feet from the agricultural implement. Other aspects may have a shorter tow beam 504 or a longer tow beam 504 depending on the shape and orientation of the conductive material of the implement. In some aspects, the tow beam 504 may be telescoping or extendable allowing the farmer to easily extend the tow beam 504 depending upon the type of agricultural implement.

Figure 6:
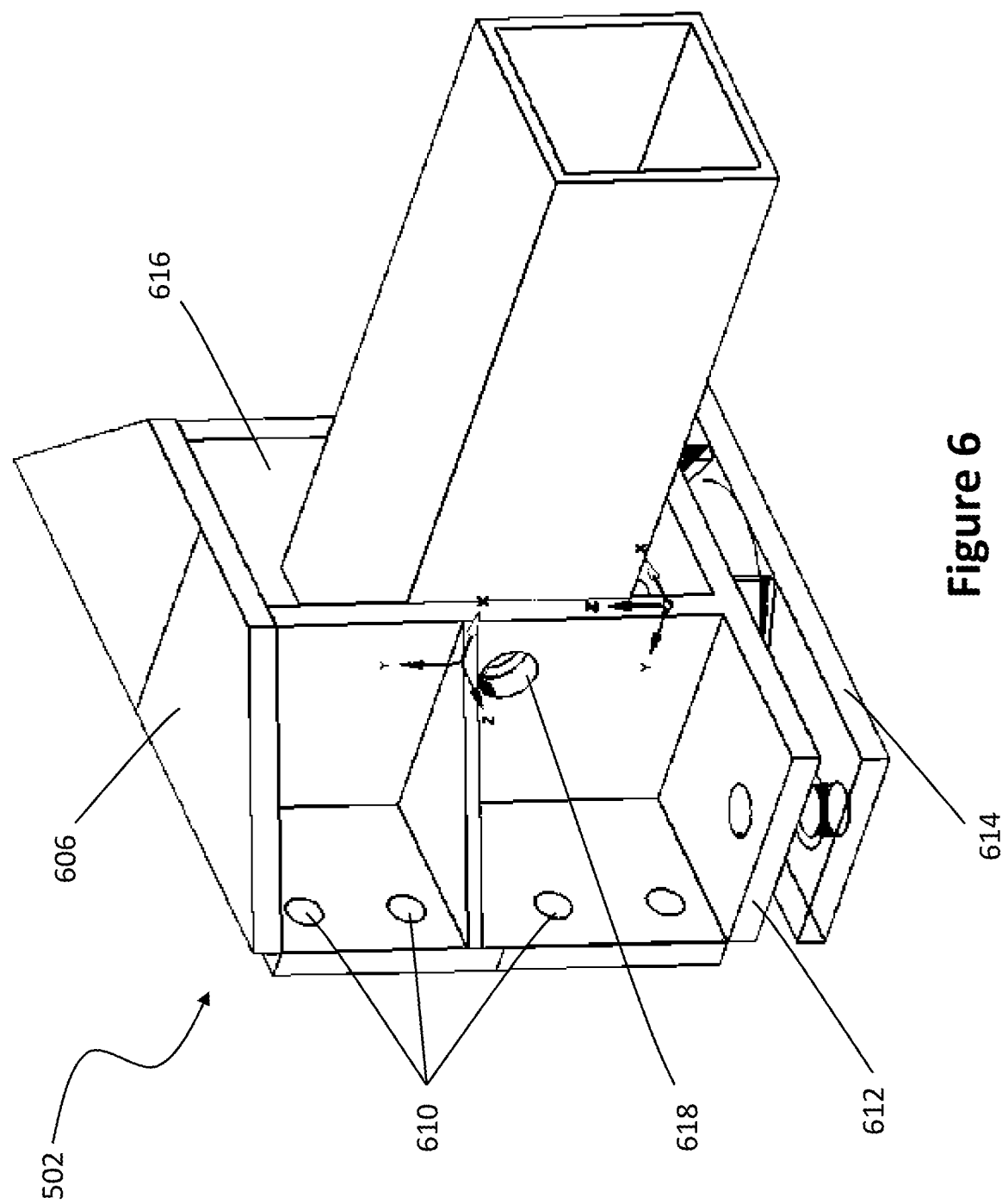
FIG. 6 is a perspective view of an attachment assembly for attaching the mapping system to the agricultural implement according to one aspect described herein.

An attachment assembly 502 as shown in FIG. 6 may affix the field mapping system to agricultural air seeder carts or toolbars. The attachment assembly 502 may be adaptable to a wide variety of implements (not shown). The attachment assembly 502 generally resembles a trapezoidal pyramid. When viewed from a top end, the attachment assembly 502 generally resembles a trapezoid 608. The base side of the trapezoid may have a plurality of bolt holes 610 along each edge for fastening the attachment assembly 502 to a rigid steel beam (not shown) on the implements, such as a rear axle beam in the case of an air, liquid, or anhydrous cart, or rear beam of a seeding toolbar. The base 612 of the attachment assembly 502 may have a hole for bolting to the hitch tab (not shown) of the implement via an adapter washer 614. The inclusion of at least two different fastening methods allows the farmer to easily affix the field mapping system to a variety of agricultural implements. The attachment assembly 502 also may comprise a recessed portion 616 for receiving the non-conductive tow beam 504. The recessed portion 616 may limit the motion of the tow beam 504 to only vertical rotational motion. A pair of holes 618 on either side of the recessed portion 616 may permit bolting or placing a pin through the non-conductive tow beam 504 to the attachment assembly 502. In some aspects, the tow beam 504 may be pivotally mounted to the attachment assembly 502 by way of a removable pin (not shown) to facilitate vertical motion of the sled 506 when the sled 506 encounters inclines and/or declines. The removable pin may enable the farmer to easily swap different lengths of tow beams 504 depending on the type of agricultural implement.

Figure 7A:
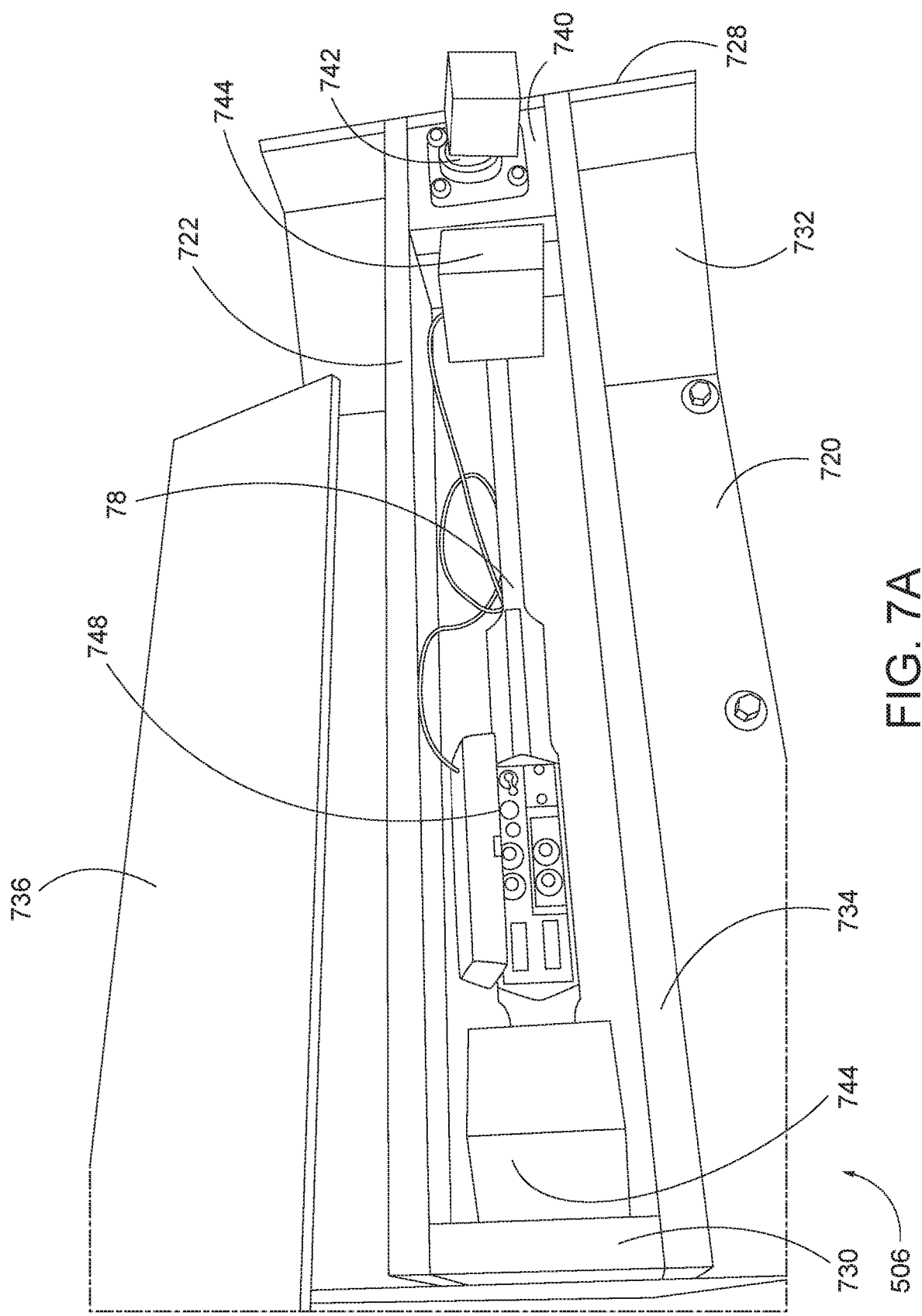
FIG. 7A is a top view photograph of a sled with a cover or lid removed.
Figure 7B:
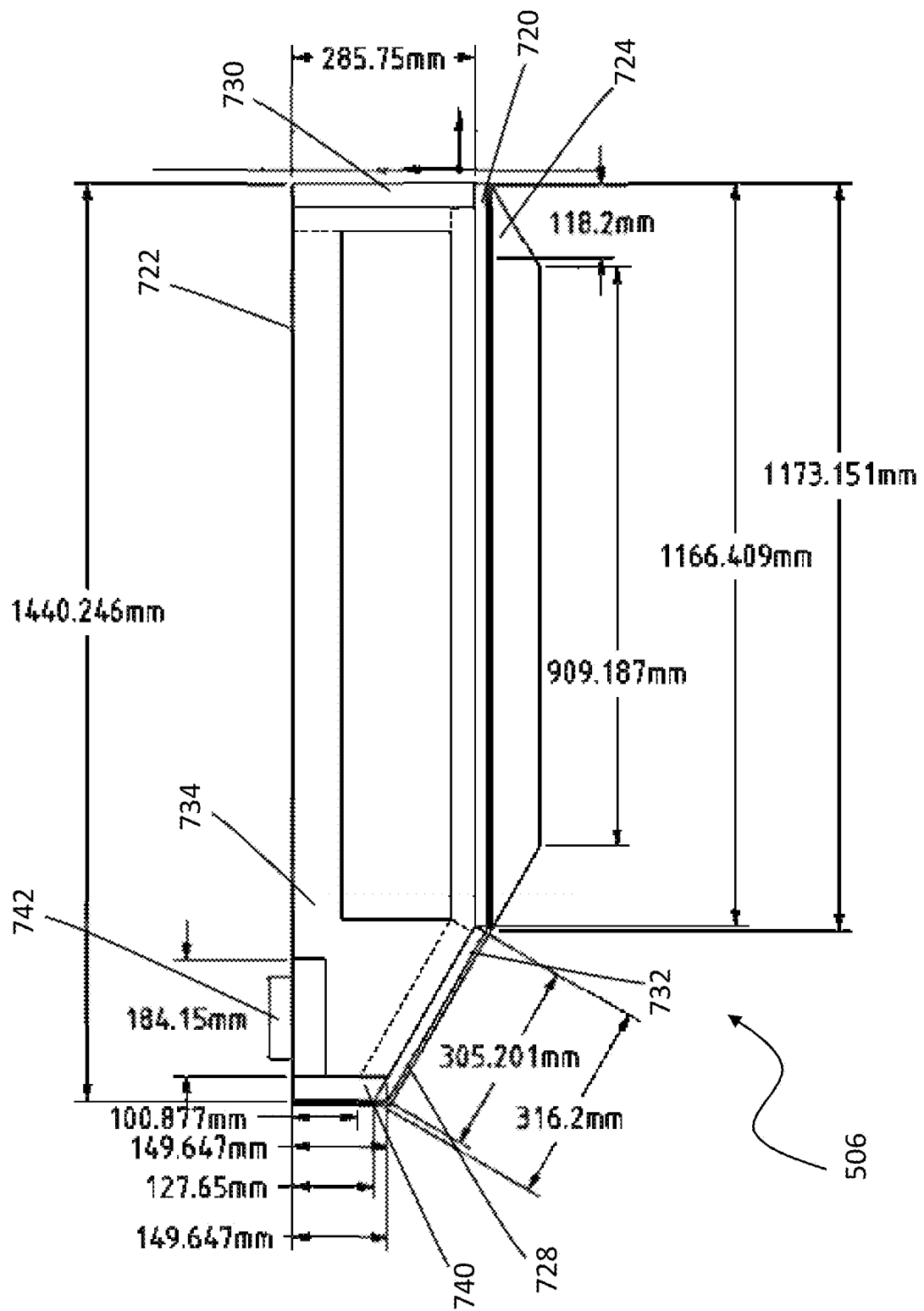
FIG. 7B is a side cross-section view of the sled.
Figure 7C:
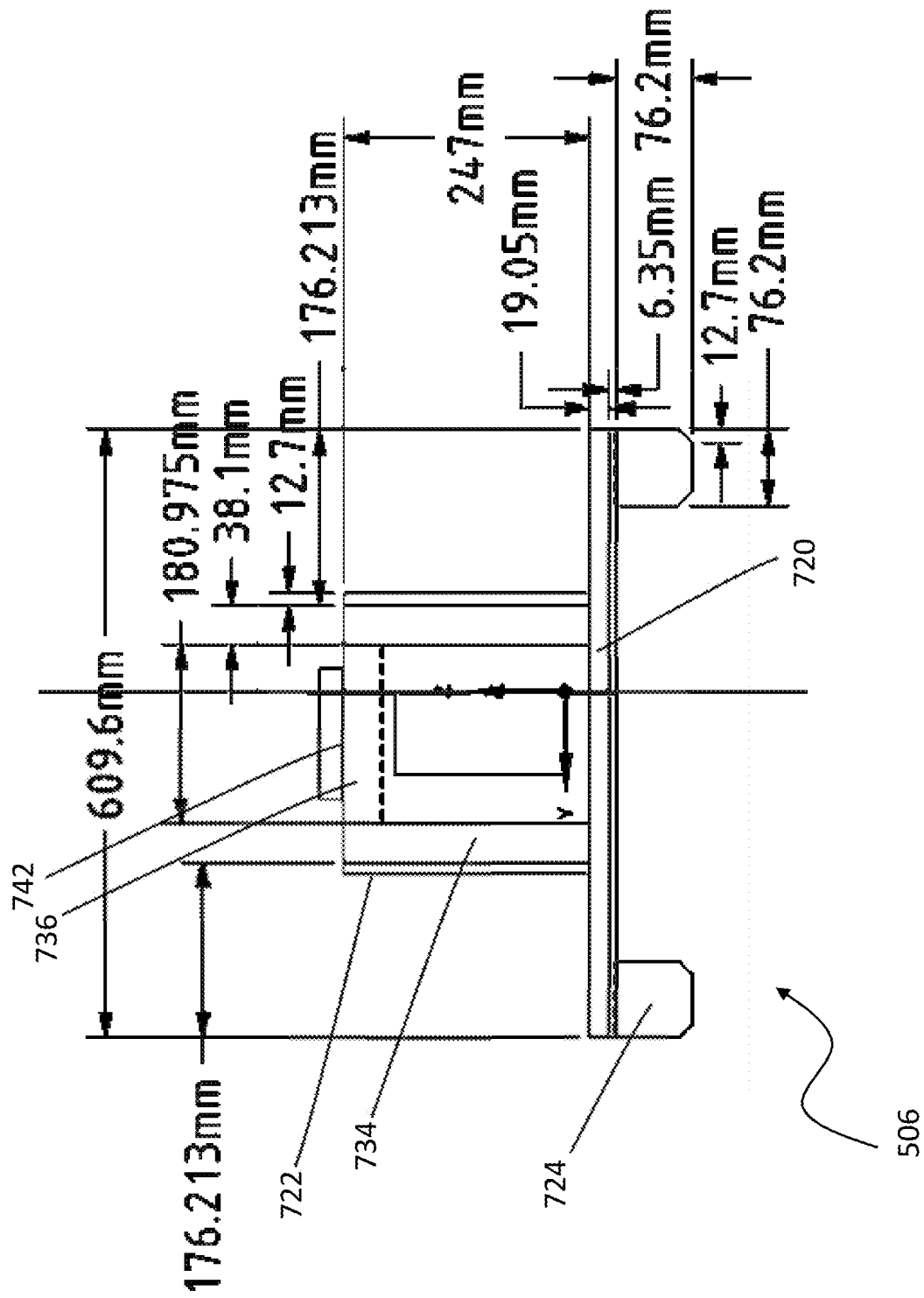
FIG. 7C is a rear cross sectional view of the sled.

Turning to FIGS. 7A to 7C, the sled 506 may be constructed of wood and/or composites. The sled 506 comprises a base 720 fastened to a housing 722. The base 720 may be approximately 1.440 m in length and approximately 0.609 m in width. A pair of skids 724 may be fastened to a bottom 726 of the base 20. The skids 724 may be approximately 7.6 cm wide and extend along either side of the base 720. The skids 724 may slope upwards towards the base 720 at a front end 728 and/or a back end 730. The skids 724 may facilitate passing the sled 506 over the field while minimizing the surface area of the sled 506 in contact with the field. In one aspect, the skids 724 may be constructed of an Ultra-High Molecular Weight (UHMW) material to act as a wear component that may be replaced when worn down from being dragged over the soil. At the front end 728 of the base 720 and the housing 722 may be a ramp 732 with a slope of between approximately 10-degrees to approximately 40-degrees configured to allow the sled 506 more easily travel over uneven terrain. The slope of the ramp 732 may generally match the slope of the front end 728 of the skids 724.

The housing 722 may have four walls 734 and may be coupled to the base 720. In other aspects, the housing 722 may be integral to the base 720. The housing 722 may have a removable cover 736. A coupler 742 may be coupled to the tow beam 504 at a front end 740 of the housing 722. In this aspect, the spherical bearing or coupler 742 may be coupled to the top of the housing 722.

In other aspects, the spherical coupler 742 may be coupled to the base 720. The spherical coupler 742 may enable the tow beam 504 to rotate with respect to the sled 506 in order to facilitate smooth turning and/or to accommodate pitch and yaw of the sled 506 over rough terrain. In other aspects, the spherical coupler 742 may be a rotatable joint and a pivotal joint for producing motion similar to the spherical coupler 742 between the sled 506 and the tow beam 504. The sled 506 may rotate 360-degrees in a horizontal plane to facilitate reversing of the implement while keeping the sled 506 at a safe distance away from the implement. In some aspects, the spherical coupler 742 may permit rotation in a vertical upward and/or downward direction.

In some aspects, the electrical wiring such as vehicular power from the tractor and/or agricultural implement may be routed through the center of the spherical coupler 742 to facilitate the 360-degree rotation of the sled 506. The electrical wiring may be secured inside the sled 506 such that any motion of the electrical wiring may not have an impact on the sensor measurements due to the wire shifting around inside the sled 506 when traversing rough fields.

In one aspect, a pair of foam bumpers 744 may be placed at either end within the housing 722 in order to protect a mapping sensor 78, such as a EM38 electrical conductivity sensor manufactured by Geonics Limited, and an electronics enclosure 748. In other aspects, the foam bumpers 744 may be a customized foam interior that matches the form of the mapping sensor 78 and the electronics enclosure 748.

During operation, while the sled 506 is being dragged across the field, the main processor 78 may sample a temperature probe (not shown). In some aspects, the temperature probe may be sampled at a rate of 1 sample per second. In other aspects, the sampling rate may be lower such as one sample per minute or one sample every 5 minutes. The main processor 67 may also receive GPS coordinates, and sample the mapping sensor 78 at a sufficient rate based on a number of factors such as vehicle velocity (e.g. 3-8 mph) and/or desired mapping resolution. In some aspects, the GPS coordinates and sampling of the mapping sensor 78 may be approximately 1-Hz. In other aspects, the GPS coordinates and sampling of the mapping sensor 78 may be in the range of 0.5 to 5-Hz. As described herein, all measurements recorded by the main processor 67 are referred to as measurement data.

In some aspects, the main processor 67 may store the measurement data within a tangible computer-readable medium (not shown) such as a Secure Digital (SD) memory card, or USB flash memory. In other aspects, the main processor 67 may stream the measurement data via a USB connection to a 3G antenna 70 to wirelessly transmit the measurement data to a web server 82. In yet another aspect, the main processor 67 may store the measurement data locally within a tangible computer-readable medium and then transmit the measurement data periodically over the 3G antenna 70 to the web server 82, such as, for example, when data costs may be lower or when the 3G antenna 70 is within range of a 3G tower (not shown). In even another alternative, the main processor 67 may wirelessly stream the measurement data via a Wi-Fi access point or Bluetooth® to an application executing on a mobile device 83. The mobile device 83 may then relay the measurement data over its own data connection. In some aspects, the main processor 67 may additionally compress and transmit the measurement data in order to save on cellular data costs and/or in order to maximize usage of the tangible computer-readable medium.

In other aspects, the application executing on the mobile device 83, 84 may connect to the Wi-Fi or Bluetooth access point provided by the main processor 67. The application may enable control of the data acquisition settings such as sampling rate, which sensor to enable, troubleshooting, diagnostics, software updates, etc. The application may also be used to access the measurement data stored within the tangible computer-readable medium.

The web server 82 may comprise a cloud storage server that enables access to the measurement data for a particular field via a laptop 84 over the Internet. The web server 82 may also comprise LIDAR data gathered by contracted fixed wing aircraft for the georeferenced field elevation and topography. The web server 82 may permit real-time or near real-time access to the measurement data being collected. The web server 82 may generally comprise a processor, memory, one or more communication interfaces, and a computer-readable medium such as a hard disk drive or the like.

The foregoing is considered as illustrative only of the principles of the invention. Further, since numerous changes and modifications will readily occur to those skilled in the art, it is not desired to limit the invention to the exact construction and operation shown and described, and accordingly, all such suitable changes or modifications in structure or operation which may be resorted to are intended to fall within the scope of the claimed invention. Although the aspects described herein are described in particular combinations, other aspects may combine the aspects in different combinations.

What is claimed is:
1. A non-conductive enclosure for a mapping system, the enclosure comprising:
    a base and at least one wall extending from the base; a removable cover received by the at least one wall;
    a foam interior for receiving at least one conductivity sensor;

a port configured to receive at least one electrical connection from an agricultural equipment, the port electrically coupled to the mapping system;

the mapping system comprising an uninterruptable power supply circuit, a power supply, at least one external sensor, and a data acquisition system; and a mounting assembly for mounting the non-conductive enclosure to the agricultural equipment.

2. The non-conductive enclosure according to claim 1, wherein the uninterruptable power supply circuit comprises an internal battery and a charger.

3. The non-conductive enclosure according to claim 1, wherein the data acquisition performs a controlled shutdown upon loss of power supplied from the agricultural equipment.

4. The non-conductive enclosure according to claim 1, wherein the power supply provides power to the at least one external sensor.

5. The non-conductive enclosure according to claim 1, wherein the external sensor provides measurement data to the data acquisition system.

6. The non-conductive enclosure according to claim 5, wherein the data acquisition stores measurement data on a tangible computer-readable medium.

7. The non-conductive enclosure according to claim 5, wherein the data acquisition system transmits the measurement data over a wireless connection to at least one computer server.

8. The non-conductive enclosure according to claim 7, further comprising at least one wireless transceiver.

9. The non-conductive enclosure according to claim 8, wherein the wireless transceiver comprises at least one of a Wi-Fi transceiver, a Bluetooth transceiver, a 3G transceiver, a 4G transceiver, an LTE transceiver, or a proprietary wireless transceiver.

10. The non-conductive enclosure according to claim 1, wherein the at least one external sensor comprises at least one of: a soil electrical conductivity sensor, at least one height sensor, a tilt sensor, and a GPS receiver.

11. The non-conductive enclosure according to claim 10, wherein the removable cover comprises a recession configured to receive the GPS receiver.

12. The non-conductive enclosure according to claim 10, further comprising an attachment to receive the at least one height sensor.

13. The non-conductive enclosure according to claim 10, wherein the mounting assembly comprises at least one support arm extending from the agricultural equipment and having the non-conductive enclosure positioned along the at least one support arm.

14. The non-conductive enclosure according to claim 13, wherein the at least one support arm is pivotally coupled to a main beam mounted horizontally with respect to the agricultural equipment.

15. The non-conductive enclosure according to claim 14, wherein the at least one support arm comprises a pair of support arms pivotally coupled on each end of the main beam.

16. The non-conductive enclosure according to claim 15, further comprising at least one shock absorber coupled between the at least one support arm and the main beam.

17. The non-conductive enclosure according to claim 16, further comprising at least one mounting bracket comprising a series of vertically arranged holes; the series of vertically arranged holes receiving one end of the at least one shock absorber; and at least one hole on the at least one support arm for receiving an other end of the at least one shock absorber.

18. The non-conductive enclosure according to claim 17, wherein a position of the sensor enclosure with respect to a soil surface and the agricultural equipment is determined by a shock absorber position of the at least one shock absorber within the series of vertically arranged holes.

19. The non-conductive enclosure according to claim 18, wherein the at least one support arm positions the sensor enclosure between about 15 cm to about 76 cm above a soil surface.

20. The non-conductive enclosure according to claim 18, wherein the at least one support arm positions the sensor enclosure between about 61 cm to about 91 cm behind the main beam.

21. The non-conductive enclosure according to claim 18, wherein the shock absorber reduces vertical acceleration and provides relief when the sensor enclosure contacts the soil surface.

22. The non-conductive enclosure according to claim 17, further comprising a hitch receiver coupled to the main beam for coupling the main beam to the agricultural equipment.

23. The non-conductive enclosure according to claim 13, wherein the at least one support arm is integrally formed with the sensor enclosure.

24. The non-conductive enclosure according to claim 13, wherein the sensor enclosure position along the at least one support arm is adjusted via a series of pins and holes along the at least one support arm.

25. The non-conductive enclosure according to claim 13, wherein the at least one support arm is pivoted fully upwards and pinned into a transport position for road travel.

26. The non-conductive enclosure according to claim 1, wherein the mounting assembly is extendable.

27. The non-conductive enclosure according to claim 1, wherein the mounting assembly comprises a non-conductive tow beam rotatably coupled to the agricultural implement at one end using an attachment assembly; and a sled coupled to the non-conductive tow beam at another end via a spherical coupler.

28. The non-conductive enclosure according to claim 27, further comprising electrically coupling a vehicular power source to the mapping system though the spherical coupler.

29. The non-conductive enclosure according to claim 27, wherein the attachment assembly resembles a trapezoidal pyramid.

30. The non-conductive enclosure according to claim 29, wherein the attachment assembly further comprises a recessed portion along the trapezoidal pyramid for receiving the non-conductive tow beam.

31. The non-conductive enclosure according to claim 30, wherein the recessed portion limits motion of the non-conductive tow beam to a vertical rotational motion.

32. The non-conductive enclosure according to claim 27, wherein the sled further comprises at least two skids fastened to a bottom of the base.

33. The non-conductive enclosure according to claim 27, wherein the spherical coupler permits the sled to rotate 360-degrees in a horizontal plane to facilitate reversing of the agricultural implement.

34. A non-conductive enclosure for a mapping system, the enclosure comprising:

a base and at least one wall extending from the base; a removable cover received by the at least one wall;

a foam interior for receiving at least one conductivity sensor;

a port configured to receive at least one electrical connection from an agricultural equipment, the port electrically coupled to the mapping system;

the mapping system comprising a power supply, at least one external sensor, and a data acquisition system;

the at least one external sensor comprising at least one height sensor and at least one of: a soil electrical conductivity sensor, a tilt sensor, and a GPS receiver; and a mounting assembly for mounting the non-conductive enclosure to the agricultural equipment.

35. The non-conductive enclosure according to claim 34, wherein the power supply comprises an uninterruptable power supply circuit.

36. The non-conductive enclosure according to claim 35, wherein the uninterruptable power supply circuit comprises an internal battery and a charger.

37. The non-conductive enclosure according to claim 34, wherein the data acquisition performs a controlled shutdown upon loss of power supplied from the agricultural equipment.

38. The non-conductive enclosure according to claim 34, wherein the power supply provides power to the at least one external sensor.

39. The non-conductive enclosure according to claim 34, wherein the external sensor provides measurement data to the data acquisition system.

40. The non-conductive enclosure according to claim 39, wherein the data acquisition stores measurement data on a tangible computer-readable medium.

41. The non-conductive enclosure according to claim 39, wherein the data acquisition system transmits the measurement data over a wireless connection to at least one computer server.

42. The non-conductive enclosure according to claim 41, further comprising at least one wireless transceiver.

43. The non-conductive enclosure according to claim 42, wherein the wireless transceiver comprises at least one of a Wi-Fi transceiver, a Bluetooth transceiver, a 3G transceiver, a 4G transceiver, an LTE transceiver, or a proprietary wireless transceiver.

44. The non-conductive enclosure according to claim 34, wherein the removable cover comprises a recession configured to receive the GPS receiver.

45. The non-conductive enclosure according to claim 34, further comprising an attachment to receive the at least one height sensor.

46. The non-conductive enclosure according to claim 34, wherein the mounting assembly is extendable.

47. The non-conductive enclosure according to claim 34, wherein the mounting assembly comprises at least one support arm extends from the agricultural equipment and having the non-conductive enclosure positioned along the at least one support arm.

48. The non-conductive enclosure according to claim 47, wherein the at least one support arm is pivotally coupled to a main beam mounted horizontally with respect to the agricultural equipment.

49. The non-conductive enclosure according to claim 48, wherein the at least one support arm comprises a pair of support arms pivotally coupled on each end of the main beam.

50. The non-conductive enclosure according to claim 49, further comprising at least one shock absorber coupled between the at least one support arm and the main beam.

51. The non-conductive enclosure according to claim 50, further comprising at least one mounting bracket comprising a series of vertically arranged holes; the series of vertically arranged holes receiving one end of the at least one shock absorber; and at least one hole on the at least one support arm for receiving an other end of the at least one shock absorber.

52. The non-conductive enclosure according to claim 51, wherein a position of the sensor enclosure with respect to a soil surface and the agricultural equipment is determined by a shock absorber position of the at least one shock absorber within the series of vertically arranged holes.

53. The non-conductive enclosure according to claim 52, wherein the at least one support arm positions the sensor enclosure between about 15 cm to about 76 cm above a soil surface.

54. The non-conductive enclosure according to claim 52, wherein the at least one support arm positions the sensor enclosure between about 61 cm to about 91 cm behind the main beam.

55. The non-conductive enclosure according to claim 51, further comprising a hitch receiver coupled to the main beam for coupling the main beam to the agricultural equipment.

56. The non-conductive enclosure according to claim 47, wherein the at least one support arm is integrally formed with the sensor enclosure.

57. The non-conductive enclosure according to claim 47, wherein the sensor enclosure position along the at least one support arm is adjusted via a series of pins and holes along the at least one support arm.

58. The non-conductive enclosure according to claim 47, wherein the at least one support arm is pivoted fully upwards and pinned into a transport position for road travel.

* * * * *